(12) United States Patent
Cohen et al.

(10) Patent No.: US 7,815,578 B2
(45) Date of Patent: Oct. 19, 2010

(54) METHODS AND APPARATUS FOR DETERMINING CARDIAC OUTPUT

(75) Inventors: Richard J. Cohen, Chestnut Hill, MA (US); Ramakrishna Mukkamala, Lansing, MI (US); Derin A. Sherman, Cedar Rapids, IA (US)

(73) Assignees: Massachusetts Institute of Technology, Cambridge, MA (US); Board of Trustees of Michigan State University, East Lansing, MI (US)

( * ) Notice: Subject to any disclaimer, the term of this patent is extended or adjusted under 35 U.S.C. 154(b) by 2101 days.

(21) Appl. No.: 10/667,956

(22) Filed: Sep. 22, 2003

(65) Prior Publication Data

US 2004/0158163 A1    Aug. 12, 2004

Related U.S. Application Data

(60) Provisional application No. 60/446,385, filed on Feb. 10, 2003.

(51) Int. Cl.
    *A61B 5/02* (2006.01)
(52) U.S. Cl. ..................................... 600/526; 600/500
(58) Field of Classification Search ................. 600/513, 600/526, 301, 483, 500
    See application file for complete search history.

(56) References Cited

U.S. PATENT DOCUMENTS

| | | | | |
|---|---|---|---|---|
| 4,429,701 A | 2/1984 | Goor et al. | ................... | 128/713 |
| 5,101,828 A | 4/1992 | Welkowitz et al. | .......... | 128/668 |
| 5,183,051 A | 2/1993 | Kraidin et al. | ............... | 128/687 |

(Continued)

OTHER PUBLICATIONS

Aboy, et al., "Automatic Detection Algorithm for Physiologic Pressure Signal Components", *Proc. 2nd Joint EMBS/BMES Conference* 2002: 196-197.

(Continued)

*Primary Examiner*—Mark W Bockelman
(74) *Attorney, Agent, or Firm*—Harness, Dickey & Pierce, P.L.C.

(57) ABSTRACT

The present invention provides methods and apparatus for determining a dynamical property of the systemic or pulmonary arterial tree using long time scale information, i.e., information obtained from measurements over time scales greater than a single cardiac cycle. In one aspect, the invention provides a method and apparatus for monitoring cardiac output (CO) from a single blood pressure signal measurement obtained at any site in the systemic or pulmonary arterial tree or from any related measurement including, for example, fingertip photoplethysmography.

According to the method the time constant of the arterial tree, defined to be the product of the total peripheral resistance (TPR) and the nearly constant arterial compliance, is determined by analyzing the long time scale variations (greater than a single cardiac cycle) in any of these blood pressure signals. Then, according to Ohm's law, a value proportional to CO may be determined from the ratio of the blood pressure signal to the estimated time constant. The proportional CO values derived from this method may be calibrated to absolute CO, if desired, with a single, absolute measure of CO (e.g., thermodilution). The present invention may be applied to invasive radial arterial blood pressure or pulmonary arterial blood pressure signals which are routinely measured in intensive care units and surgical suites or to noninvasively measured peripheral arterial blood pressure signals or related noninvasively measured signals in order to facilitate the clinical monitoring of CO as well as TPR.

14 Claims, 10 Drawing Sheets

U.S. PATENT DOCUMENTS

| | | | | |
|---|---|---|---|---|
| 5,400,793 | A | 3/1995 | Wesseling | 128/672 |
| 5,423,322 | A | 6/1995 | Clark et al. | 128/672 |
| 5,535,753 | A | 7/1996 | Petrucelli et al. | 128/672 |
| 6,368,284 | B1 | 4/2002 | Bardy | 600/508 |
| 6,485,431 | B1 | 11/2002 | Campbell | 600/526 |

OTHER PUBLICATIONS

Antonelli, et al., "Wavelet Transform Analysis of the Arterial Pressure Signal", *Computers in Cardiology*, 1994: 568-571.

Antonutto, et al., "Assessment of Cardiac Output from Noninvasive Determination of Arterial Pressure Profile in Subjects at Rest", *Eur. J. Appl. Physiol.* 69: 183-188, 1994.

Appel, et al., "Beat-to-Beat Variability in Cardiovascular Variables: Noise or Musice?", *J. Am. Coll. Cardiol.*, 14: 1139-1148, 1989.

Bourgeois, et al., "Characteristics of Aortic Diatolic Pressure Decay with Application to Continous Monitoring of Changes in Peripheral Resistance", *Circ. Res.*, 35: 56-66, 1974.

Bourgeois, et al., "Continuous Determination of Beat-to-Beat Stroke Volume from Aortic Pressure Pulses in the Dog", *Circ. Res.*, 39(1): 15-24, 1976.

Brubakk, A., "Use of Simulation Model for Estimating Cardiac Output from Aortic Pressure Curves", *Med & Biol. Eng. & Comput.*, 16: 697-706, 1978.

Cerutti, et al., "Beat-to Beat Stroke Volume Estimation from Aortic Pressure Signal in Conscious Rats: Comparison of Models", *Am. J. Physiol.*, 281: H1148-H1155, 2001.

Cibulski, et al., "Pressure Methods for Estimating Right and Left Ventricular Stroke Volumes", *Am. J. Physiol.*, 225(6): 1460-1466, 1973.

Connors, et al., "The Effectiveness of Right Heart Catheterization in the Initial Care of Critically Ill Patients", *JAMA*, 276(11):889-897, 1996.

Cundick, et al., "Clinical Comparison of Pressure-Pulse and Indicator-Dilution Cardiac Output Determination", *Circulation*, 62(2): 371-376, 1980.

Ehlers, et al., "Cardiac Output Measurements. A Review of Current Techniques and Research", *Ann. Biomed. Eng.*, 14(3): 219-239, 1986.

Fry, et al., "Measurement of Pulsatile Blood Flow by the Computed Pressure-Gradient Technique", *IRE Trans. Med. Electron., ME.* 6: 259-264, 1959.

Fry, et al., "A Catheter Tip Method for Measurement of the Instantaneous Aortic Blood Velocity", *City Res.*, 4: 627-632, 1956.

Gratz, et al., "Continuous Noninvasive Cardiac Output as Estimated from the Pulse Contour Curve", *J. Clin. Monit.*, 8:20-27, 1992.

Greenfield, et al., "Relationship Between Instantaneous Aortic Flow and the Pressure Gradient", *Cir Res.*, 17: 340-348, 1965.

Haffty, et al., "Noninvasive Tracking of Peripheral Resistance by Ear Densitography", *Chest*, 83(5); 771-775, 1983.

Hamilton, et al., "The Measurement of the Stroke Volume from the Pressure Pulse", *Am. J. Physiol.*, 148(14): 14-24, 1947.

Harley, et al., "Pressure-Flow Studies in Man: Evaluation of the Duration of the Phases of Systole", *J. Clin. Invest.*, 48: 895-905, 1969.

Herd, et al., "Arterial Pressure Pulse Contours During Hemmorrhage in Anesthetized Dogs", *J. Appl. Physiol.*, 21(6): 1864-1868, 1966.

Houtman, et al., "Non-Invasive Cardiac Output Assessment During Moderate Exercise: Pulse Contour Compared with co2 Rebreathing", *Clin. Physiol.*, 19: 230-237, 1999.

Imholz, et al., "Fifteen Years Experience with Finger Arterial Pressure Monitoring: Assessment of the Technology", *Cardiovasc. Res.*, 38: 605-616, 1998.

Jones, et al., "Velocity of Blood Flow and Stroke Volume Obtained from the Pressure Pulse", *J. Clin. Invest.*, 38: 2087-2090, 1959.

Kenner, T., "Arterial Blood Pressure and its Measurement" *Basic Res. Cardiol.*, 83(2): 107-121, 1988.

Kouchoukos, et al., "Estimation of Stroke Volume in the Dog by Pulse-Contour Method", *Cir. Res.*, 26: 611-623, 1970.

Levett, et al., "Thermodilution Cardiac Output: A Critical Analysis and Review of the Literature", *J. Surg. Res.*, 27: 392-404, 1979.

Linton, et al., "Estimation of Changes in Cardiac Output from the Arterial Blood Pressure Signal in the Upper Limb", *Br. J. Anaesth.*, 86: 486-496, 2001.

Martin, et al., "Application of Pattern Recognition and Image Classification Techniques to Determine Continuous Cardiac Output from the Arterial Pressure Signal", *IEEE Trans. Biomed. Eng.*, 41(10): 913-920, 1994.

McDonald, D.A., "Left Ventricular Output Derived from the Time-Derivative and Phase Velocities of the Aortic Pressure Wave", *Med. Biol. Eng.*, 11(6): 678-690, 1973.

Navakatiyan, et al., "A Real-Time Algorithm for the Quantification of Blood Pressure Signals", *IEEE Trans. Biomed. Eng.*, 49(7): 662-670, 2002.

Nichols, et al., "Continuous Cardiac Output Derived from the Aortic Pressure Signal: A Review of Current Methods", *Biomed. Eng.*, 8(9): 376-379, 1973.

Osborn, et al., "The Measurement of Relative Stroke Volume from Aortic Pulse Contour Pulse Pressure", *Vasc. Dis.*, 5(3): 165-177, 1968.

Perrott, et al., "An Efficient Approach to Arma Modeling of Biological Systems with Multiple Inputs and Delays", *IEEE Trans. Biomed. Eng.*, 43(1): 1-14, 1996.

Redling, et al., "Noninvasive Cardiac Output Estimation: A Preliminary Study", *Biol. Cybern.*, 77: 111-122, 1997.

Remington, et al., "The Construction of A Theoretical Cardiac Ejection Curve from the Contour of the Aortic Pressure Pulse", *Am. J. Physiol.*, 144: 546-556, 1945.

Robin, E.D., "Death by Pulmonary Artery Flow-Directed Catheter (Editorial). Time for a Moratorium?", *Chest*, 92(4): 727-731, 1987.

Starmer, et al., "Evaluation of Several Methods for Computing Stroke Volume from Central Aortic Pressure", *Circ. Res.*, 33: 139-148, 1973.

Starr, et al., "Studies Made by Simulating Systole at Necropsy. Iv. on the Relation Between Pulse Pressure and Cardiac Stroke Volume, Leading to a Clinical Method of Estimating Cardiac Output from Blood Pressure and Age", *Circulation*, 9: 648-663, 1954.

Tajimi, et al., Evaluation of Pulse Contour Methods in Calculating Stroke Volume from Pulmonary Artery Pressure Curve (Comparison with Aortic Pressure Curve). *Eur. Heart J.*, 4: 502-511, 1983.

Verdouw, et al., "Stroke Volume from Central Aortic Pressure? A Critical Assessment of the Various Formulae as to Their Clinical Value", *Basic Res. Cardiol.*, 70: 377-389, 1975.

Warner, et al., "The Role of Computers in Medical Research", *JAMA*, 196: 944-949, 1966.

Warner, et al., "Quantitation of Beat-toBeat Changes in Stroke Volume from the Aortic Pulse Contour in Man", *J. Appl. Physiol*, 5: 495-507, 1953.

Welkowitz, et al., "Noninvasive Estimation of Cardiac Output", *IEEE Trans. Biomed. Eng.*, 38(11): 1100-1105, 1991.

Wellstead, et al., "Least-Squares Indentification of Closed-Loop Systems", *Int. J. Control*, 21(4): 689-699, 1975.

Womersley, J.R., "Method for the Calculation of Velocity, Rate of Flow and Viscous Drag in Arteries When the Pressure Gradient is Known", *J. Physiol.*, 127: 553-563, 1955.

Gerhardt et al., "Non-invasive estimation of cardiac output in critical care patients," J. Clin. Monit., 16:263-268, 2001.

Hallock and Benson, "Studies on the elastic properties of human isolated aorta," Am. J. Physiol., 16: 595-602, 1937.

MacDonald, "The relation of pulsatile pressure to flow in arteries," J. Physiol, 127: 533-552, 1955.

Wesseling et al., "Computation of aortic flow from pressure in humans using a nonlinear, three-element model," Am. J. Physiol., 74(5): 2566-2573.

Wesseling et al., "A simple device for the continuous measurement of cardiac output. its model basis and experimental verification," Adv. Cardiovasc. Phys., 5: 16-52, 1983.

Ljung, L., "System Identification: Theory for the User," PTR Prentice Hall, Englewood Cliffs, N.J., 1987 (pp. 41-42 and pp. 329-338).

Webster, J.G., "Measurement of flow and volume in blood," in J.G. Webster, editor, "Medical Instrumentation. Application and Design," Houghton Mifflin, Boston, 1992 (pp. 370-374).

Guyton, A.C., "Textbook of Medical Physiology," W.B. Sanders Co., Philadelphia, 1976 (pp. 216-220).

METHODS AND APPARATUS FOR DETERMINING CARDIAC OUTPUT

CROSS-REFERENCE TO RELATED APPLICATION

This application claims priority to U.S. Provisional Patent Application 60/446,385, filed Feb. 10, 2003, which is hereby incorporated by reference.

GOVERNMENT SUPPORT

This invention was made with government support under Contract Number NAGS-4989, awarded by the National Aeronautics and Space Administration (NASA). The government has certain rights in this invention.

BACKGROUND OF THE INVENTION

Cardiac output (CO) is defined to be the volume of blood ejected by the heart per a unit time. Since CO also represents the total flow of blood supplying all the tissue beds of the body, it is perhaps the most indicative quantity of the state of the heart and circulation. CO is routinely measured in intensive care units and surgical suites in order to monitor and guide therapy for critically ill patients. These patients include, for example, those in shock (e.g., cardiogenic, hemorrhagic, or septic) or heart failure and those during and after surgery (e.g., coronary artery bypass grafting or heart valve replacement.)

An ideal CO measurement technique would be simple to perform, inexpensive, noninvasive or minimally invasive and safe, and very accurate. However, none of the conventional measurement techniques known in the art possess all of these characteristics [10]. For example, the thermodilution technique, which is currently employed in most intensive care units and surgical suites, involves injecting cold saline into the right atrium and measuring the temperature downstream in the pulmonary artery. The average CO over the measurement period may than be computed from conservation of mass laws. Although the technique is relatively simple and inexpensive, it requires an invasive right heart catheterization whose safety is questionable [8,38] and is not very accurate due to the many assumptions upon which it is based (e.g., no saline recirculation and thorough blood mixing) [10,27]. The most accurate, conventional technique for measuring CO involves surgically implanting a flow probe, either electromagnetic or ultrasonic, directly on the aorta. Although this technique also provides a continuous measurement of CO, it requires a high risk thoracotomy which is rarely performed in practice. Moreover, the accuracy of the aortic flow probe is highly dependent on vessel preparation and may only be accurate to within about 15-20 percent [10,27].

Although the development of an ideal CO measurement technique has proven to be difficult, several ideal, or near ideal, techniques are currently available for the continuous measurement of peripheral arterial blood pressure such as Finapres technology [23] and arterial tonometry [25]. Previous investigators have therefore sought techniques to monitor CO from peripheral arterial blood pressure signals. The most popular techniques in the art are the so-called pulse contour methods that assume the arterial tree to be well represented by a parallel combination of a capacitor and resistor thereby accounting for the compliance of the large arteries (AC) and the total peripheral resistance (TPR) of the small arteries. If the instantaneous CO supplied by the heart is represented as a current source, then the simple model of the heart and arterial tree in FIG. 1A results. Most of these types of pulse contour methods are specifically based on mathematical formulas which are derived by making simplifying assumptions and approximations to this model (see, for example, [7, 19-21, 26, 40, 43, 44]). These methods have generally failed to yield good correlation between CO determined from analysis of ABP signals and directly measured CO over a wide range of physiologic conditions [39, 42].

Bourgeois et al. [3,4] did successfully demonstrate that their pulse contour method when applied to an ABP signal measured centrally in the aorta could yield a quantity which varied linearly with directly measured CO (electromagnetic aortic flow probe) over a wide range of physiologic conditions. Their method, which makes no simplifying assumptions or approximations to the model of FIG. 1A, may be explained as follows. During the diastolic period of each cardiac cycle, the heart is filling and not supplying blood to the arterial tree (see FIG. 1B). Thus, according to the model, ABP decays with a time constant $\tau_D$ equal to the product of TPR and AC during each diastolic period (see FIG. 1B). Since AC is essentially constant over a wide pressure range and on the time scale of days [4, 18,37], CO could then be monitored to within a constant scale factor (equal to the reciprocal of AC) by dividing the ABP by $\tau_D$.

Bourgeois et al. specifically demonstrated that beat-to-beat CO may be monitored from $\tau_D$ and the governing differential equation of the model of FIG. 1A. Thus, a key step of the pulse contour method of Bourgeois et al. is to fit an exponential to the diastolic decay portion of an ABP wavelet in order to measure $\tau_D$. Osborn et al. [34] introduced essentially the same method prior to Bourgeois et al. but their experimental validation was not as complete or compelling.

Bourgeois et al. were able to validate their pulse contour method with respect to a canine ABP signal measured centrally in the aorta, because the diastolic portion of such a signal usually resembles an exponential decay (see FIG. 2A). These investigators specifically identified the position in the aorta at the level of the dorsal insertion of the diaphragm as the optimal site for observing an exponential diastolic decay. However, Bourgeois et al. acknowledged that central ABP is rarely obtained clinically because of the difficulty in inserting a catheter retrogradely via a peripheral arterial blood vessel and the risk of blood clot formation and embolization. Moreover, they recognized that, in peripheral ABP signals which are routinely made available in intensive care units and surgical suites usually via a more simple and safe radial artery catheterization, an exponential diastolic decay is usually not apparent (see FIG. 2B). The method of Bourgeois et al. therefore cannot generally be applied to readily available peripheral ABP signals. In fact, its application to central ABP signals may be somewhat limited, as Cundick et al. [9] reported that they could not identify an optimal location in the human aorta in which the diastolic portion of the ABP signal appeared as a pure exponential decay.

Other pulse contour methods that are based on more complex representations of the arterial tree have also been developed (see, for example, [5, 11, 12, 16, 24, 31-33, 50]). However, these techniques required the analysis of one, or even two, central ABP signals. Thus, their clinical utility is also severely limited.

Several techniques have more recently been introduced in an attempt to monitor CO from ABP signals measured peripherally. Techniques based on an adaptive aorta model which require ABP signals measured at two peripheral sites—the carotid artery and the femoral artery—have been developed [36, 46]. However, catheters are usually not placed for prolonged periods of time at either of these sites in intensive care units or surgical suites due to issues of safety. Another previous technique is based on an empirically-derived formula which involves the calculation of the derivative of the ABP signal [14]. However, in order to mitigate the corruptive effects of wave reflections on the derivative calculation, this technique also requires two peripheral ABP measurements, one of which is obtained from the femoral artery. Other techniques based on a learning approach have been previously proposed [6, 15, 30]. However, these techniques require extremely large sets of training data consisting of simultaneous measurements of CO and ABP signals obtained over the entire range of physiologic conditions. Moreover, the success of these techniques was only demonstrated with central ABP signals or only over a narrow physiologic range. Finally, Wesseling et al. [1, 48, 49] and Linton and Linton [28] have recently proposed model-based techniques which require only the analysis of a single radial artery pressure signal. However, Linton and Linton showed that their technique was reasonably accurate only over a narrow range of physiologic conditions, and several previous studies have demonstrated the inadequacy of the method of Wesseling et al. (see, for example, [13, 22]).

It is evident that there remains a need in the art for methods and apparatus for determining CO reliably and accurately using information obtained from the arterial blood pressure signal. In particular, there remains a need in the art for methods and apparatus for determining CO reliably and accurately using information obtained from the peripheral arterial blood pressure signal.

SUMMARY OF THE INVENTION

The present invention addresses this need, among others. In one aspect, the invention provides for the measuring of a physiologic signal indicative of cardiovascular system activity, e.g., an arterial blood pressure (ABP) signal over a plurality of cardiac cycles. From analysis of the arterial blood pressure signal or other physiological signal the times of the cardiac contractions are identified. Then the relationship between the times of the cardiac contractions and the physiologic signal over a plurality of cardiac cycles is mathematically analyzed. From this analysis a mathematical relationship between the occurrence of the cardiac contraction at a certain time and the subsequent time evolution of the arterial blood pressure over a time period greater than one cardiac cycle is obtained. This mathematical relationship is then used to determine a dynamical property of the system. For example, in one preferred embodiment the mathematical relationship is the impulse response function between the occurrence of cardiac contractions and the arterial blood pressure signal. In one preferred embodiment the dynamical property is the time constant which describes the decay of the impulse response function over a time interval, e.g., a time interval such as between 2 and 4 seconds following the maximum height of the exponential. In another preferred embodiment the dynamical property is the impulse response function itself.

In particular, in a preferred embodiment the invention provides a method and apparatus for monitoring CO by analyzing the long time scale variations (greater than a cardiac cycle) in a single ABP signal, which may be obtained at any site in the systemic or pulmonary arterial tree. The present invention determines TD through the analysis of long time intervals (60-90 second intervals in a preferred embodiment) of an ABP signal according to the following three steps (see FIG. 3). The first step involves constructing an impulse train signal, x(t), in which each impulse is located at the start of a cardiac contraction and has an area equal to the ensuing arterial pulse pressure (or an arbitrary constant value in another preferred embodiment). The constructed signal therefore approximately reflects cardiac contractions in terms of timing and output (or just timing, in those embodiments in which the area of the impulses is an arbitrary constant).

The second step deals with determining the dynamical properties of the arterial tree through the characterization of the relationship between the cardiac contractions and the ABP signal. This is achieved by estimating an impulse response function (h(t)) which when convolved with x(t) best fits the ABP signal (y(t)), according to any of a number of criteria. The estimated h(t) represents a normalized ABP response to a single cardiac contraction. The final step involves fitting an exponential to the tail end of the diastolic decay portion of the estimated h(t) in which the faster wave reflections have vanished in order to determine $\tau_D$. Accurate determination of $\tau_D$ is achieved by virtue of h(t) coupling the long time scale variations in x(t) to y(t).

The present invention, which in a preferred embodiment includes an analog-to-digital converter, a buffer system, a signal processing unit, and a display and alarm system (see FIG. 4), may thus be utilized to monitor CO and/or TPR, to within constant scale factors from any measured ABP signal despite the presence of wave reflections. Note that absolute CO and/or TPR of the systemic or pulmonary arterial tree (depending on the signal measurement site) may also be determined, if desired, by calibration with a single, absolute measure of CO such as a thermodilution measurement.

The present invention may be employed in intensive care units and surgical suites in which invasive radial ABP signals are routinely available and pulmonary ABP signals are sometimes available. The present invention may also be applied to noninvasively measured peripheral ABP signals (e.g., Finapres technology, arterial tonometry) or noninvasively measured signals related to ABP (e.g., fingertip photoplethysmography [45], ear densitography [17]). Thus, the present invention could easily be employed in primary care settings, emergency rooms, and regular hospital beds in order to facilitate the evaluation of the patient's heart and circulatory state.

This application refers to various patents and publications. The contents of all of these are incorporated by reference.

DETAILED DESCRIPTION OF CERTAIN PREFERRED EMBODIMENTS OF THE INVENTION

The present invention encompasses the recognition that there is significant information present in the ABP signal when measured over long time scales (greater than a single cardiac cycle), and that this information, referred to herein as "long time scale information", may be used to facilitate determination of dynamical properties of the systemic or pulmonary arterial tree.

Long time scale information incorporates information reflecting the variability of the ABP signal between beats in addition to, or instead of, reflecting only information about the ABP signal within single beats. Although long time scale information is acquired by measuring the ABP signal over a period greater than a single cardiac cycle (typically seconds to minutes), not all quantities derived from measurements performed over time periods greater than a single cardiac cycle include long time scale information. For example, it is common to measure ABP over a plurality of cardiac cycles and average the measured amplitudes to obtain mean (average) ABP. However, mean ABP does not incorporate long time scale information, because it contains no information reflecting the variability between beats. Once an average value is found (e.g., by integrating the ABP signal over a time interval and dividing by the length of the time interval), information reflecting differences in length and/or amplitude of the ABP signal is lost. Thus the mean ABP does not incorporate long time scale information.

Capturing the information present over long time scales offers a number of advantages for the determination of dynamical properties of the systemic or pulmonary arterial tree. In particular, utilizing such information provides a means of accurately determining such properties through measurement of the ABP signal, despite the fact that the ABP signal (particularly the peripheral ABP signal) is corrupted by wave reflections that occur at sites of impedance mismatch (e.g., vessel bifurcations).

Figure 1A:
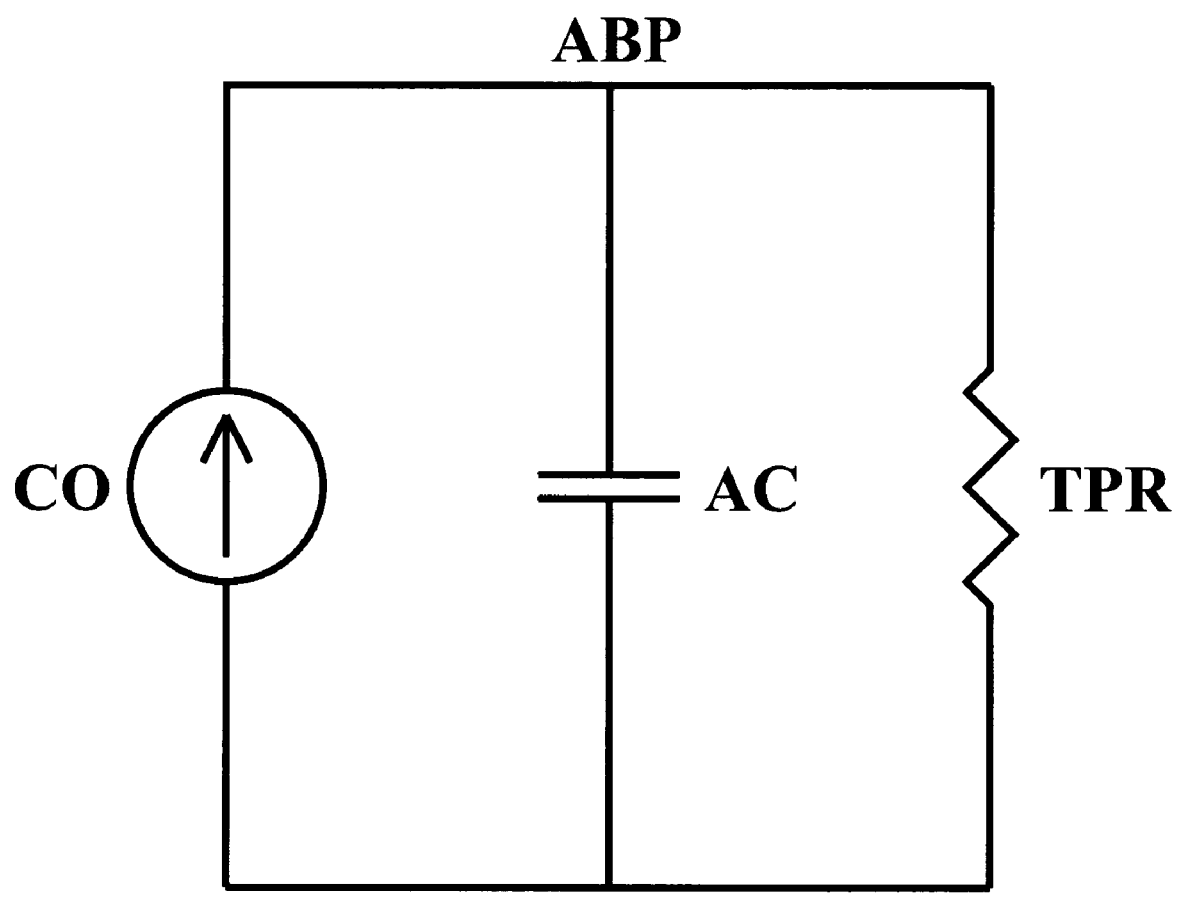
FIG. 1A is a simple, lumped model of the heart and arterial tree (either systemic or pulmonary). CO is cardiac output; ABP, arterial blood pressure; TPR, total peripheral resistance; and AC, arterial compliance.
Figure 1B:
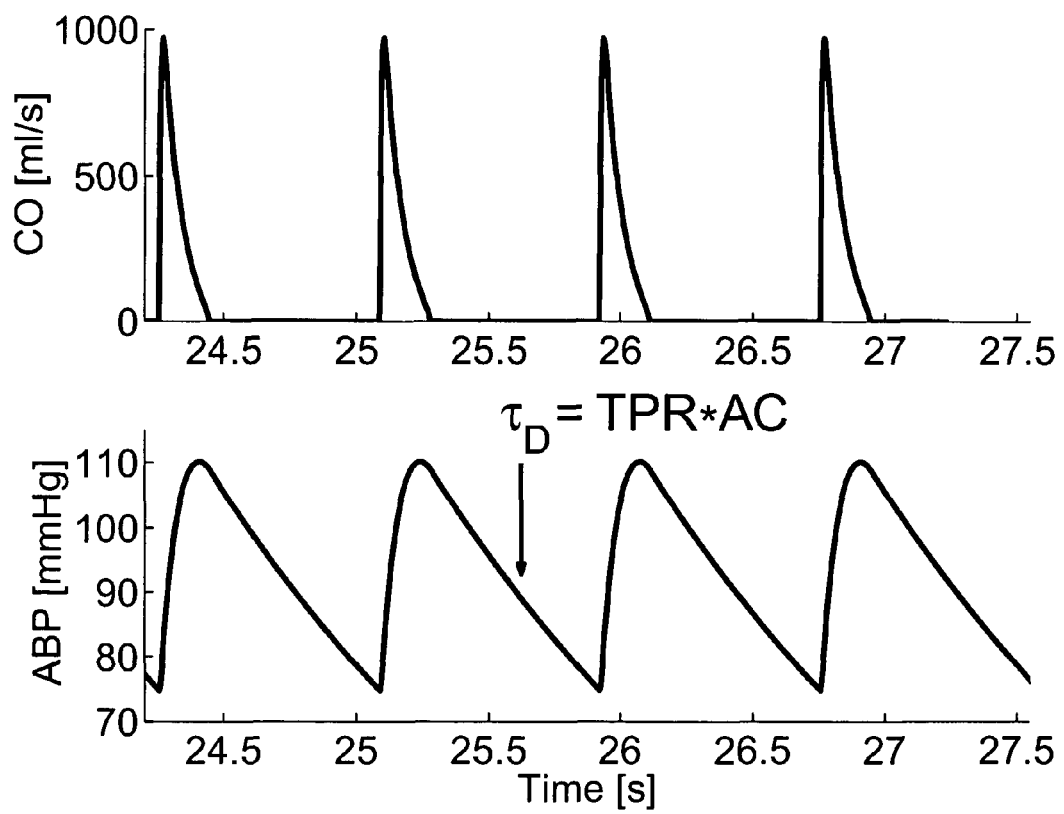
FIG. 1B is a plot of a realistic, continuous CO signal and a plot of the ABP signal response to the CO signal determined according to the simple model of FIG. 1A. The time constant $\tau_D$ governs the dynamical behavior of the simple model.

The inventors have recognized that at sufficiently long time scales, the wavelengths of the propagating waves may be longer than the dimension of the arterial tree. Thus the wave reflections corrupt peripheral ABP signals, but only on relatively short time scales which, however, may exceed the duration of a single cardiac cycle, leaving the signal on longer time scales relatively undisturbed. This implies that the lumped model in FIG. 1A is a valid representation of the long time scale dynamics of the arterial tree (either systemic or pulmonary) despite its limitations as an accurate representation of the arterial tree over single cardiac cycles. Moreover, the arterial tree is continuously being excited at time scales greater than a cardiac cycle by ongoing perturbations (e.g., breathing) and the dynamic, compensatory response of the regulatory system (e.g., arterial baroreflex) [2]. Thus significant long time scale information is generally present in ABP signals, and the present invention utilizes this information to provide methods for determining dynamical properties of the systemic or pulmonary arterial tree.

The invention provides a method for determining a dynamical property of the systemic or arterial tree comprising steps of: (a) measuring a physiologic signal over a plurality of cardiac cycles; (b) obtaining a relationship between the timing of a cardiac contraction and the evolution of the physiologic signal over a time period greater than that of a single cardiac contraction cycle by analyzing the physiologic signal over a plurality of cardiac cycles; and (c) using the relationship to determine the dynamical property. In general, the physiologic signal is a signal indicative of cardiovascular system activity. For example, in certain embodiments of the invention the physiologic signal is an arterial blood pressure (ABP) signal. In certain embodiments of the invention the physiologic signal is a signal related to the ABP signal. Such related signals include, but are not limited to, pressure signals obtained using fingertip photoplethysmography [45], ear densitography [17], etc. In certain embodiments of the invention the physiologic signal is the arterial-systemic filling pressure difference (ASFPD). For purposes of description, the invention will be described in terms of the ABP signal, but it is to be understood that other physiologic signals may be similarly used.

In general, a dynamical property of a system is a characteristic of the system that relates to how the system responds over time to a change in one or more of the parameters of the system. For example, a mathematical expression that relates future values of one or more signals generated by a system to past and present values of signals either sensed or generated by the system would constitute a dynamical property of the system. A characteristic time is also a dynamical property. In general, a characteristic time indicates the time scale of the temporal evolution of a function. (For example, for an exponential function given by $y(t)=e^{-t/\tau}$, the time constant $\tau$ is a characteristic time of the function.)

In particular an impulse response function which enables one to compute the expected future values of a signal generated by the system from past values of that signal or past values of other signals either generated or sensed by the system would constitute a dynamical property of the system. The characteristic time of the decay of that impulse response function would also be a dynamical property of the system. Note that the dynamical property need not fully predict how the system responds over time to a change in one or more of the parameters of the system, rather it need only be descriptive of the response. Dynamical properties of systems can often be estimated from analysis of signals associated with the system.

The relationship between the timing of a cardiac contraction and the evolution of the ABP signal over time may be obtained in a number of different ways. Determination of one or more dynamical properties of the systemic or pulmonary arterial tree in turn allows one to obtain values for a variety of important parameters that characterize the cardiovascular system, including, but not limited to, cardiac output, total peripheral resistance, cardiac index, stroke volume, characteristic time constant, etc.

One application of the methods described above is in measuring cardiac output (CO). The invention provides a method of determining cardiac output to within a constant scale factor comprising steps of: (a) measuring a physiologic signal over a plurality of cardiac contraction cycles; (b) estimating a function that represents the response of the physiologic signal to a cardiac contraction over a time period greater than that of a single cardiac cycle; (c) determining a characteristic time of the function; (d) determining cardiac output to within a constant scale factor by dividing the magnitude of the physiologic signal by the characteristic time obtained in step (c). The invention further provides a method of determining total peripheral resistance to within a constant scale factor comprising steps of: (a) measuring a physiologic signal over a plurality of cardiac contraction cycles; (b) estimating a function that represents the response of the physiologic signal to a cardiac contraction over a time period greater than that of a single cardiac cycle; and (c) determining a characteristic time of the function, wherein total peripheral resistance is given to within a constant factor by the characteristic time.

In certain embodiments of the invention rather than determining the characteristic time of the function estimated in part (b) of the above methods, a second function that represents the response of a different physiologic signal to a cardiac contraction over a time period greater than that of a single cardiac contraction is estimated, and the characteristic time of this second function is determined and used in step (d). Accordingly, the invention provides a method of determining cardiac output to within a constant scale factor comprising steps of: (a) measuring a first physiologic signal over a plurality of cardiac contraction cycles; (b) measuring a second physiologic signal over a plurality of cardiac contraction cycles; (c) estimating a function that represents the response of the second physiologic signal to a cardiac contraction over a time period greater than that of a single cardiac cycle; (d) determining a characteristic time of the function; and (e) determining cardiac output to within a constant scale factor by dividing the magnitude of the first physiologic signal by the characteristic time obtained in step (d). The methods will now be described in more detail.

A feature common to the techniques discussed above for monitoring CO from continuous ABP is that the signal analysis is considered only within individual cardiac cycles. Because of the presence of wave reflections at these time scales, these techniques are limited in that they 1) can only be applied to central ABP signal in which the cumulative effects of the pulse reflections are largely attenuated; 2) necessitate two peripheral ABP signal measurements which are not usually obtained clinically; 3) require a large set of training data obtained over a wide range of physiologic conditions, or 4) are reasonably accurate only over a limited physiologic range.

Figure 2A:
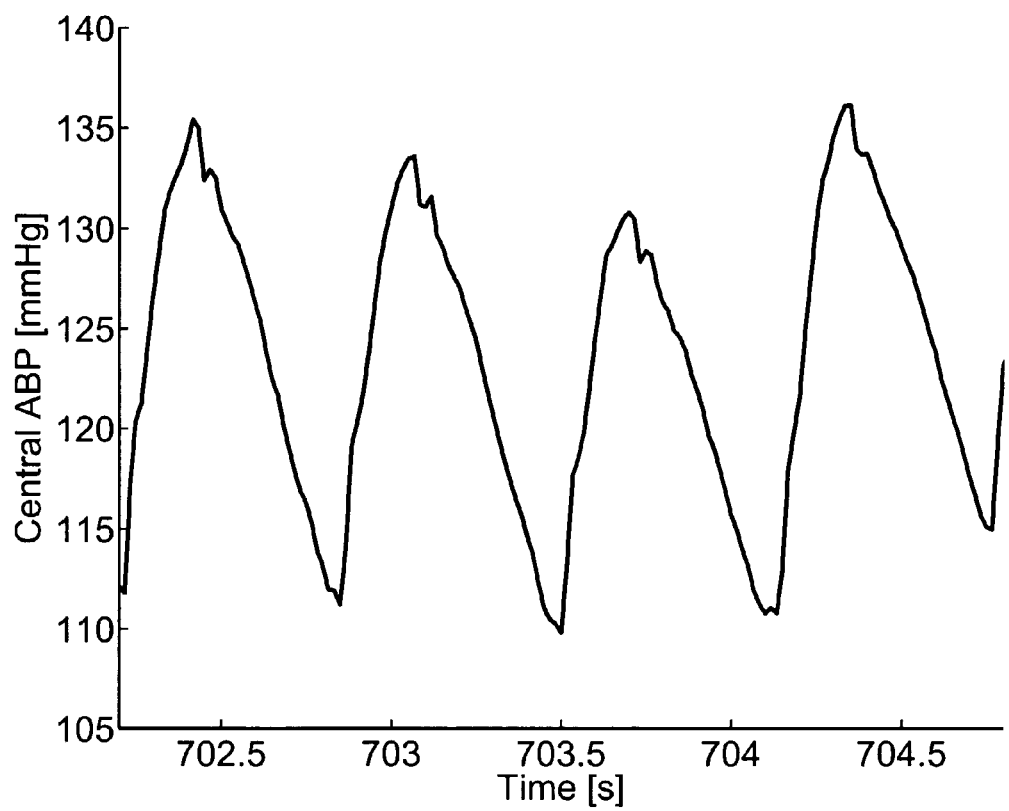
FIG. 2A is an example of a central ABP signal measured in an experimental sheep preparation.
Figure 2B:
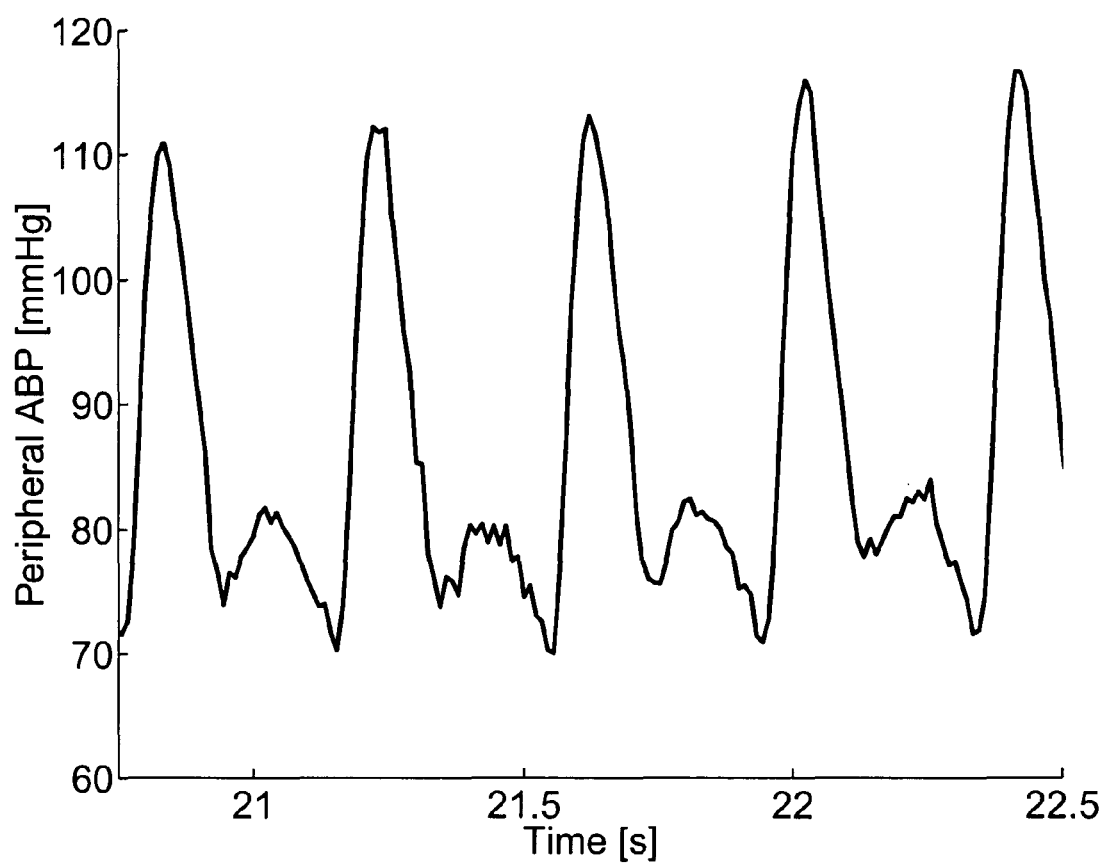
FIG. 2B is an example of a peripheral ABP signal measured in the brachial artery of an experimental dog preparation.

In particular, methods that attempt to determine CO by measuring the time constant ($\tau_D$) of the arterial tree, which could then be used to compute CO to within a constant scale factor (equal to the reciprocal of AC) have had only limited success for the following reasons. In peripheral ABP signals such as those typically available in intensive care units and surgical suites via a technique such as radial artery catheterization (and also peripheral ABP signals obtained via non-invasive techniques such as fingertip photoplethysmography or ear densitography), an exponential decay is not usually apparent (see FIG. 2B). This is because, as mentioned above, the arterial tree is not a lumped system but actually a distributed system with impedance mismatches throughout the system due to vessel tapering and bifurcations as well as changes in vessel caliber. Thus the diastolic portion (as well as the systolic portion) of peripheral ABP signals is corrupted by wave reflections that occur at each site of impedance mismatch. (Note that the complexity of these sites as well as their varying distances from the aorta result in reflected waves with large phasic differences which generally tend to mitigate the cumulative effects of these waves on the central ABP signal.) Even in the case of central APB signals it may not be possible to identify an optimal location in the human aorta at which the diastolic portion of the ABP signal appears as a pure exponential decay [9]. Similarly, efforts to locate a suitable position in the pulmonary arterial tree in which the diastolic portions of the pulmonary ABP signal appear as an exponential decay have been unsuccessful [41].

Thus the presence of wave reflections has impeded development of accurate methods to determine the time constant of the arterial tree, which could then be employed to compute CO. As described below, the present invention overcomes this difficulty through the use of long time scale information to accurately estimate $\tau_D$, from which CO may then be determined using the following formula:

$$CO = \frac{(ABP)(AC)}{\tau_D}$$

The scale factor, AC, for a particular individual may be determined by obtaining a single absolute measurement of CO, e.g., by thermodilution, and then solving for AC in the above formula using the estimated value for TD. Alternately, AC may be estimated using tables or nomograms, which are well known in the art and may be based on parameters such as age, weight, height, or particular disease status (see, e.g., U.S. Pat. No. 6,485,431). Additional parameters such as total peripheral resistance (TPR), cardiac index, stroke volume (SV), etc., may also be determined using well known relationships. For example, TPR=($\tau_D$)/AC, TPR=ABP/CO, and SV=(CO)/heart rate.

The CO signal estimated from the formula given above will reflect true CO over time periods greater than or equal to a single cardiac cycle, but will generately not accurately reflect the cardiac flow signal within a single cardiac cycle. For this reason, it may be desirable to average the ABP signal or the estimated CO signal over each cardiac cycle. Alternatively, in certain embodiments of the invention the ABP signal or estimated CO signal is filtered using a low-pass filter with a characteristic response time greater than the duration of a typical cardiac cycle. Another alternative is to simply average the ABP signal or estimated CO signal over a time period longer than the duration of a typical cardiac cycle (multibeat averaging). In general, a single-beat average approach or by use of a low-pass filter with a fairly short characteristic time would be expected to retain the most information regarding time variation of the CO signal as compared with simple averaging of the CO signal over long time periods. The time constant $\tau_D$ changes slowly in time (because over a time scale of tens of seconds peripheral resistance is slowly varying and the arterial compliance AC may be regarded as essentially constant), however the cardiac output itself can vary much more rapidly—on a beat-to-beat basis. Thus it is generally preferable to estimate the CO from the formula given above together with use of a single beat average or low-pass filtering approaches—even if the constant $\tau_D$ is estimated from long epochs of data comprising perhaps tens of seconds—as opposed to simple averaging over time scales long compared to the duration of a single cardiac cycle.

Although absolute CO may be determined using the formula given above, one important aspect of the invention is the recognition that in many circumstances it is not necessary to obtain a value for absolute CO. For example, in the context of continuous monitoring in the acute setting (e.g., in intensive care units), it is changes in CO rather than absolute CO that is most clinically relevant. Thus determination of the proportionality constant is unnecessary, and this potential source of error may thus be avoided. In other words, the present invention may be used to monitor CO (e.g., identify and quantify changes in CO) instead of (or in addition to) determining absolute CO.

According to the method of the invention an analog ABP signal is measured invasively or noninvasively at any site in the systemic or pulmonary arterial tree. The analog signal is quantized and sampled. For example, in a preferred embodiment of the method the signal is quantized at 12 bits and sampled at 90 Hz. It is noted that these values are exemplary only, and one of ordinary skill in the art will readily be able to select other appropriate values. A signal representing cardiac contractions is constructed through the formation of an impulse train in which each impulse is located at the start of a cardiac contraction and has an area equal to the ensuing arterial pulse pressure, i.e., the pulse pressure that results from that cardiac contraction (see FIG. 3). The start of each cardiac contraction is determined by detecting the onset of the upstroke of each ABP wavelet, which may be done by any of a variety of methods known in the art, e.g., those described in [51], [52], or [53]. The arterial pulse pressure for each wavelet is given by the difference in the maximum value of ABP and the value of ABP at the onset of the upstroke.

Alternatively, the area of each impulse may be set to an arbitrary constant value. In another preferred embodiment, a surface electrocardiogram (ECG) is measured simultaneously with the ABP signal. The two signals are quantized at 12 bits and sampled at 360 Hz. It is noted that these values are exemplary only, and one of ordinary skill in the art will readily be able to select other appropriate values. The start of each cardiac contraction may then be established by detecting each R-wave of the ECG. In certain embodiments of the invention the constructed impulse train and ABP signal are then decimated, e.g., for purposes of noise reduction. For example, in one embodiment of the invention the constructed impulse train and ABP signal are decimated from 360 Hz to 90 Hz.

Figure 3:
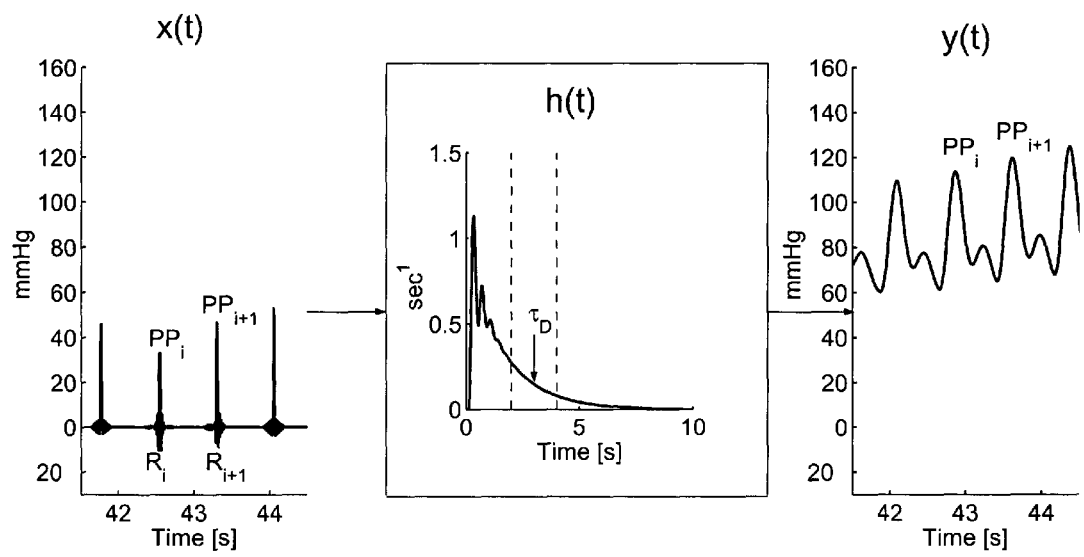
FIG. 3 is an illustration of how one embodiment of the present invention determines $\tau_D$ from a peripheral ABP signal. PP is arterial pulse pressure; R, the time of the R-wave in a surface electrocardiogram; x(t), an impulse train signal representing cardiac contractions; y(t), an ABP signal; and h(t), the impulse response which when convolved with x(t) best fits y(t).

The single contraction ABP response (normalized by approximately the average arterial pulse pressure when each impulse is scaled to the ensuing arterial pulse pressure), which quantitatively characterizes the dynamical properties of the arterial tree, is determined by estimating the discrete-time impulse response function (h(t)) which when convolved with the 90 Hz impulse train (x(t)) "best" fits the 90 Hz ABP signal (y(t)) in the least squares sense (see FIG. 3).

The impulse response function is assumed to be well represented by an autoregressive moving average (ARMA) model which is given below:

$$y(t) = \sum_{i=1}^{m} a_i y(t-i) + \sum_{i=1}^{n} b_i x(t-i) + e(t),$$

where e(t) is the residual error term, m and n limit the number of terms in the model (model order), and the set of parameters $\{a_i, b_i\}$ completely defines h(t) [29]. Because the ARMA model is parametric, causality may be imposed, which is necessary for reliably estimating h(t) as x(t) and y(t) are related in a closed-loop fashion (i.e., y(t) also influences x(t) through the autonomically mediated heart rate baroreflex) [47].

For a fixed model order, the set of parameters is estimated from 60-90 second intervals of x(t) and y(t) through the least-squares minimization of the residual error term, which has an analytic solution [29]. The model order is determined by an ARMA parameter reduction algorithm that penalizes for the degree of model complexity [35]. Prior to estimation of h(t), x(t) and y(t) may be lowpass filtered in order to amplify the contribution of long time scale energy such that the least squares fit between x(t) and y(t), at these time scales, is prioritized. Note that any other parametric model (e.g., autoregressive moving average with exogenous input (ARMAX) model [29]) may be employed in various embodiments of the invention to represent the structure of h(t), and any other minimization criterion (e.g., absolute error) may be utilized to find the "best" h(t). In certain embodiments of the invention the number of parameters in the model is selected at least in part based on the heart rate.

The $\tau_D$ quantity is determined by finding the "best" exponential that fits h(t) over a selected time interval following the time of the maximum value of h(t), preferably a time interval in which the faster wave reflections have become minimal. For example, as shown in the plot of h(t) presented in FIG. 3, the contribution of the faster wave reflections becomes minimal at approximately 1.5-2 seconds, as evidenced by the decrease in fluctuations of h(t). Following this time the impulse response may be accurately approximated as an exponential. Thus in certain preferred embodiments of the invention the selected time interval begins approximately 1.5 seconds following the time of maximum h(t), more preferably approximately 2 seconds following the time of maximum h(t). For example, it has been found that a time interval of 2 to 4 seconds following the time of maximum value of h(t) is suitable. Longer time intervals may also be used. Typically the appropriate time interval is predetermined, but in certain embodiments of the invention it may be selected as the measurements are being made.

The following exponential equation is the basis of the resulting least squares problem where A and $\tau_D$ are parameters to be estimated through the least squares minimization of w(t).

$$h(t) = Ae^{-t/\tau_D} + w(t),$$

By first log transforming h(t) over the interval of interest (which is always greater than zero), the optimal estimate of the parameters in the least squares sense may be estimated through an analytic linear least squares solution [4]. CO may then be computed to within a constant scale factor equal to 1/AC through the ratio of the ABP signal to $\tau_D$ as discussed above. Note that TPR of the systemic or pulmonary arterial tree (depending on the signal measurement site) is trivially given, to within a constant scale factor equal to AC, by $\tau_D$.

In the embodiment of the invention described above proportional CO is determined by dividing ABP by $\tau_D$. In another embodiment of the invention, rather than employing ABP, the method uses the arterial-systemic filling pressure difference (ASFPD). The ASFPD is determined by subtracting systemic venous pressure from arterial blood pressure [54]. The systemic filling pressure can either be measured, or more commonly estimated. All the analyses described above can then be performed on the ASFPD rather than on the ABP signal, including estimation of the cardiac output. In this embodiment the ASFPD is divided by the time constant to obtain a signal proportional to cardiac output.

This embodiment of the invention offers a number of potential advantages. In the absence of cardiac contractions the arterial blood pressure would decay over time to the systemic filling pressure, thus it is not fully accurate to describe the decay of the ABP impulse reponse function at long times as an exponential that decays to zero. However, since in the absence of cardiac contractions the ASFPD does decay to zero, a description in terms of an exponential decay at long times is more appropriate for the impulse response function of the ASFPD. Furthermore, since the time constant of the impulse response function is estimated at long times when the impulse response function has already decayed substantially, even if the systemic filling pressure is small, there may be a significant difference in the decay constant estimated from the impulse response functions of the ABP compared to the ASFPD—with the analysis of the ASFPD providing a more accurate result.

Figure 4:
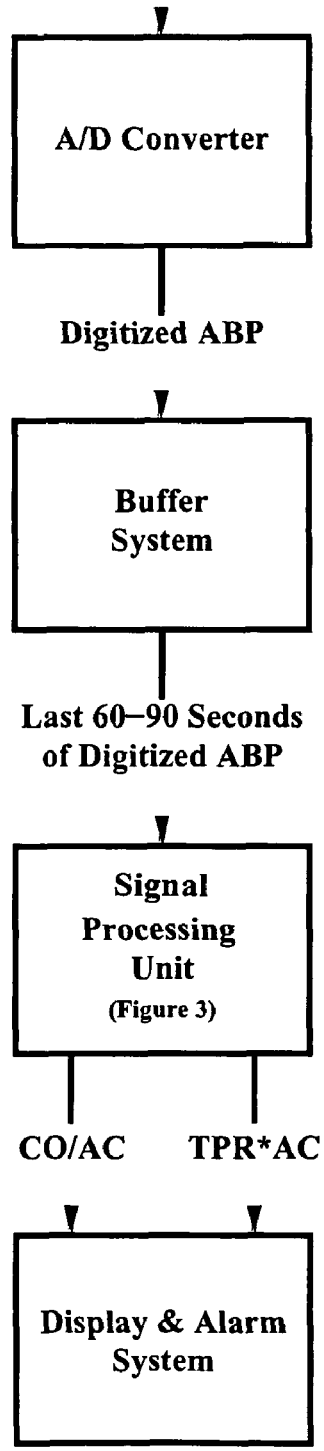
FIG. 4 is a block diagram of one embodiment of the present invention.

FIG. 4 depicts a block diagram illustrating a preferred embodiment of the present invention. An analog ABP signal is fed into an analog-to-digital converter as it is being measured. The ABP signal may be acquired using standard methods, such as those mentioned above. In certain embodiments of the invention a surface electrocardiogram is also obtained (ECG), e.g., via standard ECG leads. The digitized ABP signal is stored in a buffer system. The most recent 60-90 second intervals of the digitized signal are transferred from the buffer system to a processing unit which analyzes the signal according to FIG. 3 in order to estimate $\tau_D$. The buffer and processing unit may be implemented using, for example, any standard microcomputer running appropriate software to implement the mathematical operations described above. The software components of the invention may be coded in any suitable programming language and may be embodied in any of a ragne of computer-readable media including, but not limited to, floppy disks, hard disks, CDs, zip disks, DVD disks, etc. Outputs such as proportional CO, CO, and TPR may be displayed on a visual display such as a computer screen and/or may be printed or transmitted to a remote location. The ECG, and analysis thereof, may also be displayed. In a preferred embodiment of the system the process is continuously repeated thereby providing the on-line monitoring of CO and TPR (with a delay of 30-45 seconds). Finally, in certain embodiments of the invention an alarm is triggered upon excessive decreases in CO.

Alternatively, the AC proportionality constant may be computed with a single absolute measure of CO (e.g., thermodilution) through the product of $\tau_D$ and the measured CO divided by ABP, as discussed above. The proportionality constant AC may then be utilized to obtain absolute measures of CO and TPR. Note that physiologic changes in AC due to disease or aging may also be monitored with multiple, simultaneous measurements of absolute CO and an ABP signal.

Figure 5:
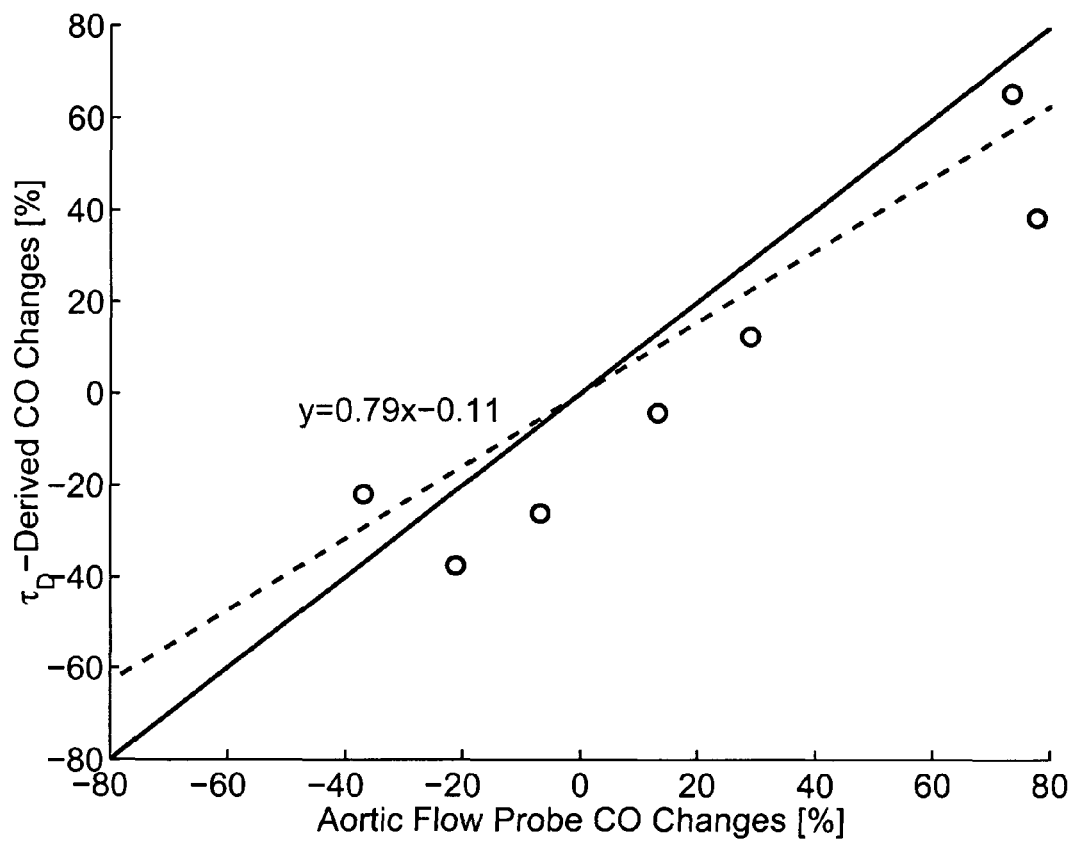
FIG. 5 is the result of a pilot experimental rabbit study which demonstrates the correspondence between relative CO changes determined from a femoral ABP signal according to the present invention and an aortic flow probe. CO was altered by various interventions (e.g., pacing, inferior vena cava balloon occlusion, and nitroglycerine). The solid line is the line of identity, and the dashed line is the line that best fits the data points.

The present invention was evaluated in a pilot study in which femoral ABP and aortic flow probe CO were simultaneously measured in an experimental rabbit preparation during various interventions known to alter CO (e.g., pacing, inferior vena cava balloon occlusion, and nitroglycerine). FIG. 5 illustrates that the resulting relative changes in CO with respect to baseline predicted by the present invention correspond to those changes determined from the aortic flow probe. In FIG. 5 the x-axis represents the percentage change in CO as measured using the aortic flow probe, while the y-axis represents the percentage change in CO as determined using the present invention. The solid line (line of identity) represents results that would be achieved by a technique that precisely replicated the aortic flow probe measurements. The dashed line represents the values measured using the present invention and demonstrates a very close fit.)

The invention was further evaluated in six experiments in swine, in which peripheral ABP signals and independent CO via an aortic flow probe were simultaneously measured over a wide physiologic range. Six Yorkshire swine (30-34 kg) were studied under a protocol approved by the MIT Committee on Animal Care. The animals were given intramuscular tiletamine-zolazepam, xylazine, and atropine prior to endotracheal intubation. The swine were then maintained in a deep plane of anesthesia with inhaled isoflorane 0.5%-4%. Positive-pressure mechanical ventilation at a rate of 10-15 breaths/min and a tidal volume of 500 ml was employed.

Physiologic transducers were placed as follows. 7.5 French sheath introducers (Arrow International, Reading, Pa.) were placed in the bilateral femoral arteries. A micromanometer-tipped catheter (SPC 350, Millar Instruments, Houston, Tex.) was fed retrograde to the thoracic aorta from the femoral artery for central ABP. The catheter was specifically positioned to achieve a diastolic decay that appeared as exponential as possible. The second introducer was attached to stiff fluid-filled tubing (Arrow International) and an external pressure transducer (TSD104A, Biopac Systems, Santa Barbara, Calif.) for femoral ABP. The chest was opened with a midline sternotomy. An ultrasonic flow probe was placed around the aortic root for gold standard CO (T206 with A-series probes, Transonic Systems, Ithaca, N.Y.). Finally, a 23- or 25-gauge angiocatheter was placed as distal as possible to the brachial artery and attached to an external pressure transducer via short, rigid tubing for "radial" ABP. Each transducer output was interfaced to a microcomputer via an A/D conversion system (MP150WSW, Biopac Systems). The data were recorded at a sampling rate of 250 Hz and 16-bit resolution.

In each animal, a subset of the following interventions was performed over the course of 75 to 150 minutes to vary CO and other hemodynamic parameters: infusions of volume, phenylephrine, dobutamine, isuprel, esmolol, nitroglycerine, and progressive hemorrhage. Several infusion rates were implemented followed by brief recovery periods.

The technique was applied off-line to six-minute intervals (overlapping by three minutes) of the digitized "radial" and femoral ABP signals to estimate $\tau$ and proportional CO trends. The corresponding gold standard CO trends were established by averaging the aortic flow probe measurements over the identical time intervals. Gold standard T trends were similarly sought by applying the technique of Bourgeois et al [4] to the central ABP signals. As a metric for comparison between an estimated trend ($\hat{X}(i)$) and the corresponding gold standard trend ($X_0(i)$), the root-mean-square-normalized-error (RMSNE) in percent was computed as follows:

$$RMSNE = \sqrt{\frac{1}{N}\sum_{i=1}^{N}\left(\frac{\hat{X}(i) - X_0(i)}{X_0(i)}\right)^2} \cdot 100\%,$$

where N represents the number of analyzed six-minute intervals and the argument i denotes the $i^{th}$ analyzed six-minute interval. In order to use this metric to compare an estimated proportional CO trend with the corresponding absolute gold standard CO trend, the former trend was first scaled to have the same mean value as the latter trend for each animal. The correlation coefficient (ρ) between the estimated and gold standard trends was also calculated as a scale-invariant metric for comparison.

Figure 6:
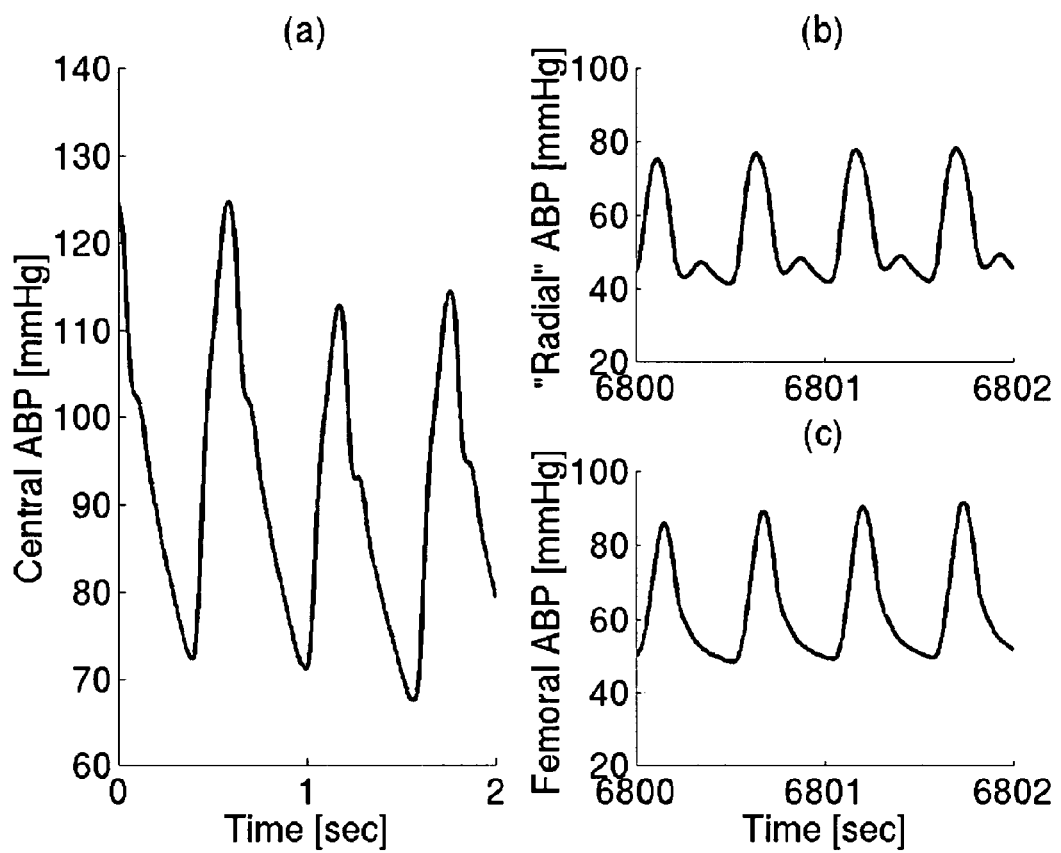
FIG. 6 shows example excerpts of measured (a) central, (b) "radial", and (c) femoral arterial blood pressure (ABP) signals from an experiment performed in swine.

FIG. 6 illustrates example excerpts of the digitized central, "radial", and femoral ABP signals. The central ABP excerpt is from the beginning of the recording period in which the aortic catheter was positioned such that the diastolic decay appeared as exponential as possible. Unfortunately, the diastolic decay of the central ABP signal did not consistently appear as a single exponential throughout the recording period in which various interventions were employed. The "radial" and femoral ABP excerpts are from the same time but later in the recording period. Although the diastolic decay of the femoral ABP excerpt appears smooth, it cannot be adequately represented by a single exponential function.

Figure 7:
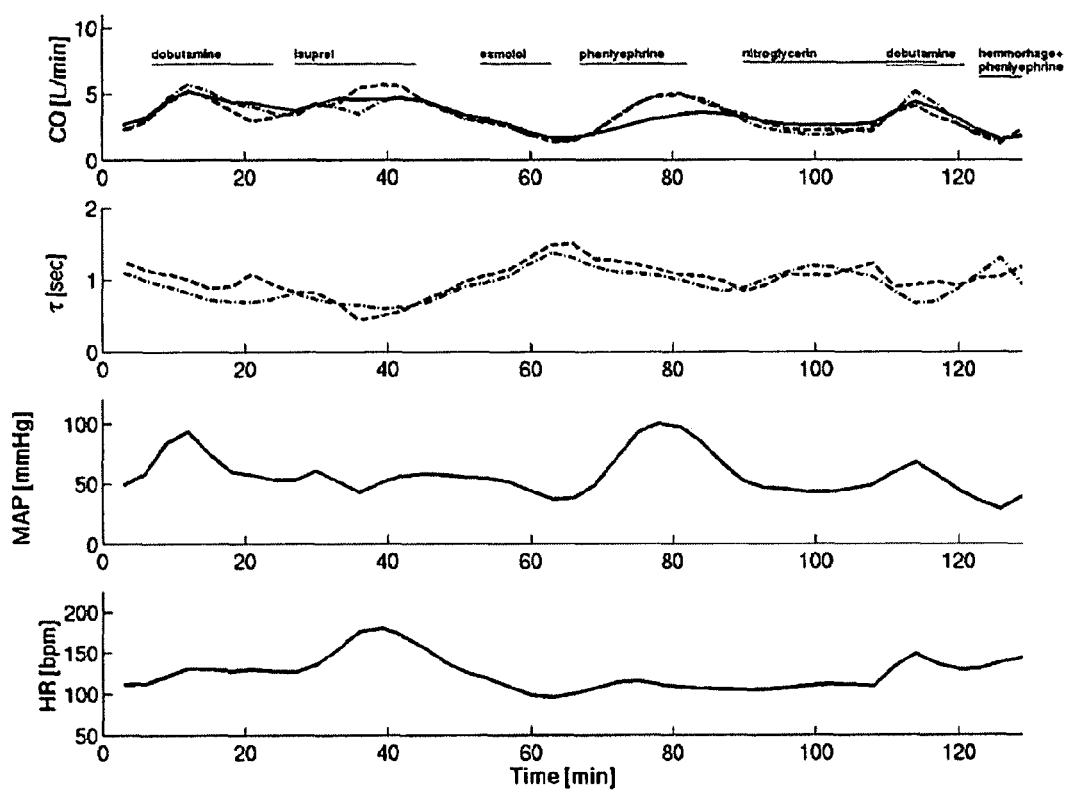
FIG. 7 presents results from animal 1 in an experiment in which the method of the invention was tested in swine. The top panel illustrates the aortic flow probe cardiac output (CO) trend (solid), estimated and calibrated CO trends from the "radial" (dash) and femoral (dash-dot) arterial blood pressure (ABP) signals, and the intervention and duration (underline). The second panel depicts $\tau_D$ trends estimated from the "radial" (dash) and femoral (dash-dot) ABP signals. The bottom two panels illustrate the mean ABP (MAP) and heart rate (HR) trends.
Figure 8:
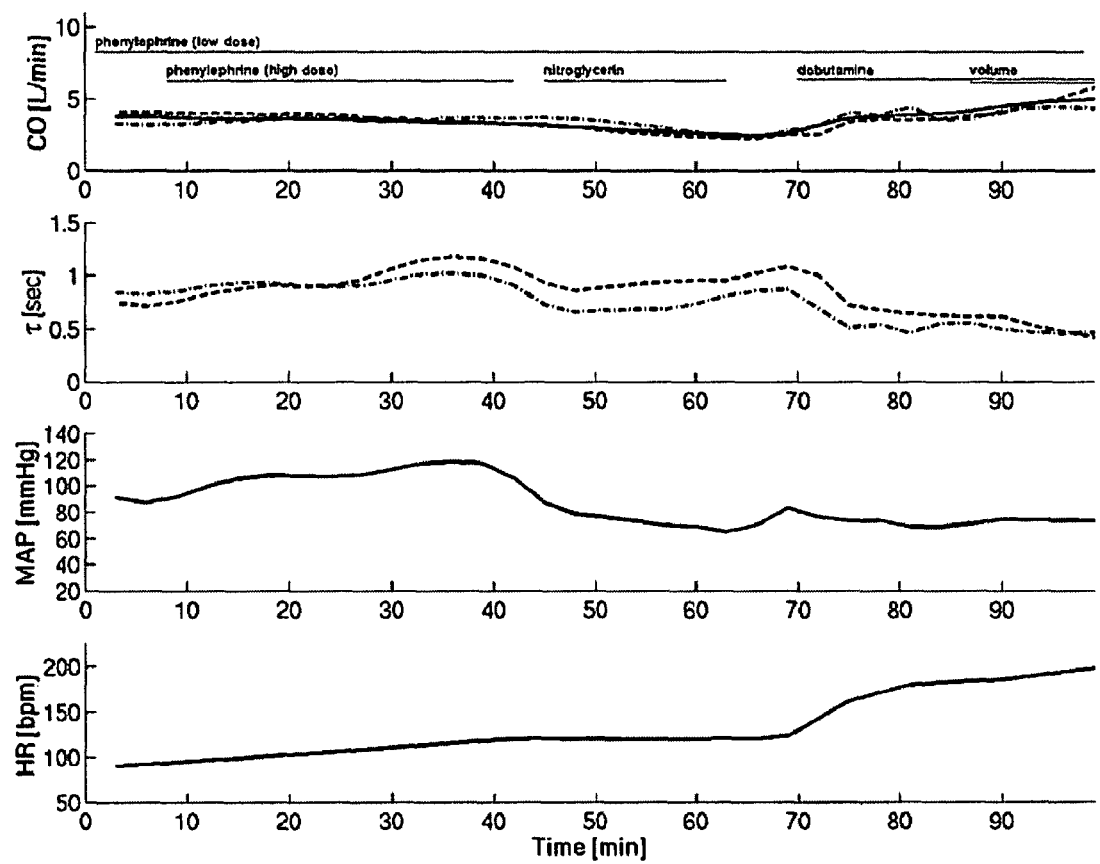
FIG. 8 present results from animal 5 in an experiment in which the method and apparatus of the invention were tested in swine. Panels correspond to those in FIG. 7.

Table 1 summarizes the results for each animal, and FIGS. 7 and 8 are examples of the corresponding trends for animal 1 (worst result) and animal 5 (best result). (The femoral ABP signal of animal 4 was not analyzed due to excessive damping.) The table and figures illustrate the wide physiologic range imposed by the interventions and strong agreement between the estimated and gold standard CO trends (in terms of CO RMSNE and visually). This strong agreement was confirmed by high overall r values (mean±SD) between the gold standard CO trends and the CO trends estimated from the "radial" (0.84±0.07) and femoral (0.86±0.05) ABP signals. Additionally, Table 2 shows that the CO errors (difference between calibrated, estimated CO trends and corresponding gold standard CO trends) were largely uncorrelated with CO, mean ABP (MAP), and heart rate (HR).

The low overall $\tau_D$ RMSNE in the table is buttressed by a high overall ρ value (mean±SD) between the two $\tau_D$ trend estimates (0.85±0.08). Thus, there is solid agreement between the two $\tau_D$ trend estimates despite substantial differences in short-time scale morphology between the "radial" and femoral ABP signals (FIG. 6), and the overall CO measurement error is only 14.6%. Preliminary studies show that the six-minute intervals used here may be reduced to, for example, three-minute intervals without materially affecting the results.

In certain other embodiments of the invention it may be desirable to adjust the proportionality constant AC to vary depending on the arterial blood pressure or heart rate, if it is found that there is a systematic difference between dependence of the estimated cardiac output and the absolute cardiac output on heart rate or arterial blood pressure.

The foregoing description is to be understood as being representative only and is not intended to be limiting. Alternative systems and techniques for implementing the methods of the invention will be apparent to one of skill in the art and are intended to be included within the accompanying claims.

REFERENCES

[1] Antonutto, G., M. Girardis, D. Tuniz, E. Petri, and C. Capelli. Assessment of cardiac output from noninvasive determination of arterial pressure profile in subjects at rest. Eur. J. Appl. Physiol., 69:183-188, 1994.

TABLE 1

Summary of results. CO is cardiac output; MAP, mean arterial pressure; HR, heart rate; RMSNE, root-mean-square-normalized-error; and $\tau_D$ long time constant of arterial tree.

| ANIMAL | CO RANGE [L/MIN] | MAP RANGE [MMHG] | HR RANGE [BPM] | CO RMSNE [%] femoral | CO RMSNE [%] "radial" | $\tau_D$ RMSNE [%] |
|---|---|---|---|---|---|---|
| 1 | 1.6-5.2 | 29-100 | 96-180 | 19.9 | 19.1 | 8.3 |
| 2 | 2.3-4.2 | 54-127 | 101-204 | 10.2 | 16.0 | 5.9 |
| 3 | 1.9-5.8 | 70-120 | 96-186 | 8.8 | 16.7 | 14.7 |
| 4 | 1.3-4.3 | 27-106 | 103-198 | — | 12.3 | — |
| 5 | 2.4-5.0 | 65-118 | 91-198 | 10.2 | 8.0 | 9.7 |
| 6 | 2.3-5.6 | 52-108 | 109-177 | 17.1 | 14.7 | 12.4 |
| TOTAL | 1.3-5.8 | 27-127 | 91-204 | 14.0 | 15.0 | 10.3 |

TABLE 2

Correlation coefficient (ρ) matrix. ABP is arterial blood pressure. See Table 1 caption.

| | CO | MAP | HR |
|---|---|---|---|
| "RADIAL" ABP CO ERRORS | 0.11 | 0.47 | −0.08 |
| FEMORAL ABP CO ERRORS | 0.09 | 0.32 | 0.14 |

Since we were not able to obtain gold standard $\tau_D$ trends from the central ABP signals, we compared the two $\tau_D$ trends estimated from the "radial" and femoral ABP signals, which should, in theory, be equivalent. Table 1 summarizes the comparison results in terms of $\tau_D$ RMSNE in which the gold standard trends were established as the average of the two $\tau_D$ trend estimates. That is, the $\tau_D$ RMSNE here equals the root-mean-square of the difference between the two $\tau_D$ trend estimates divided by their sum and is the same for either signal.

[2] Appel, M. L., R. D. Berger, J. P. Saul, J. M. Smith, and R. J. Cohen. Beat-to-beat variability in cardiovascular variables: Noise or music? J. Am. Coll. Cardiol., 14:1139-1148, 1989.

[3] Bourgeois, M. J., B. K. Gilbert, D. E. Donald, and E. H. Wood. Characteristics of aortic diatolic pressure decay with application to the continuous monitoring of changes in peripheral resistance. Circ. Res., 35:56-66, 1974.

[4] Bourgeois, M. J., B. K. Gilbert, G. von Bernuth, and E. H. Wood. Continuous determination of beat-to-beat stroke volume from aortic pressure pulses in the dog. Circ. Res., 39(1):15-24, 1976.

[5] Brubakk, A. O. Use of a simulation model for estimating cardiac output from aortic pressure curves. Med. & Biol. Eng. & Comput., 16:697-706, 1978.

[6] Cerutti, C., M. P. Gustin, P. Molino, and C. Z. Paultre. Beat-to-beat stroke volume estimation from aortic pressure signal in conscious rats: Comparison of models. Am. J. Physiol., 281:H1148-H1155, 2001.

[7] Cibulski, A. A., P. H. Lehan, and H. K. Hellems. Pressure methods for estimating right and left ventricular stroke volumes. Am. J. Physiol., 225(6):1460-1466, 1973.

[8] Connors, A. F., T. Speroff, N. V. Dawson, C. Thomas, F. E. Harrell, D. Wagner, N. Desbiens, L. Goldman, A. W. Wu, R. M. Califf, W. J. Fulkerson, H. Vidaillet, S. Broste, P. Bellamy, J. Lynn, W. A. Knaus, and for the SUPPORT Investigators. The effectiveness of right heart catheterization in the initial care of critically ill patients. JAMA, 276(11):889-897, 1996.

[9] Cundick, R. M. and R. M. Gardner. Clinical comparison of pressure-pulse and indicator-dilution cardiac output determination. Circulation, 62(2):371-376, 1980.

[10] Ehlers, K. C., K. C. Mylrea, C. K. Waterson, and J. M. Calkins. Cardiac output measurements. a review of current techniques and research. Ann. Biomed. Eng., 14(3):219-239, 1986.

[11] Fry, D. L. Measurement of pulsatile blood flow by the computed pressure-gradient technique. IRE Trans. Med. Electron., ME-6:259-264, 1959.

[12] Fry, D. L., A. J. Mallos, and A. G. T. Casper. A catheter tip method for measurement of the instantaneous aortic blood velocity. Circ. Res., 4:627-632, 1956.

[13] Gerhardt, U. M. W., C. Scholler, D. Bocker, and H. Hohage. Non-invasive estimation of cardiac output in critical care patients. J. Clin. Monit., 16:263-268, 2001.

[14] Goor, D. and R. Mohr. Method and apparatus for measuring the systemic vascular resistance of a cardiovascular system. U.S. Pat. No. 4,429,701. Feb. 7, 1984.

[15] Gratz, I., J. Kraidin, A. G. Jacobi, N. G. de Castro, P. Spagna, and G. E. Larijani. Continuous noninvasive cardiac output as estimated from the pulse contour curve. J. Clin. Monit., 8:20-27, 1992.

[16] Greenfield, J. C. and D. L. Fry. Relationship between instantaneous aortic flow and the pressure gradient. Circ. Res., 17:340-348, 1965.

[17] Haffty, B. G., N. E. O'Hare, J. B. Singh, and D. H. Spodick. Noninvasive tracking of peripheral resistance by ear densitography. Chest, 83(5):771-775, 1983.

[18] Hallock, P. and J. C. Benson. Studies on the elastic properties of human isolated aorta. Am. J. Physiol., 16:595-602, 1937.

[19] Hamilton, W. F. and J. W. Remington. The measurement of the stroke volume from the pressure pulse. Am. J. Physiol., 148(14):14-24, 1947.

[20] Harley, A., C. F. Starmer, and J. C. Greenfield. Pressure-flow studies in man: Evaluation of the duration of the phases of systole. J. Clin. Invest., 48:895-905, 1969.

[21] Herd, J. A., N. R. Leclair, and W. Simon. Arterial pressure pulse contours during hemorrhage in anesthetized dogs. J. Appl. Physiol., 21(6):1864-1868, 1966.

[22] Houtman, S., B. Oeseburg, and M. T. Hopman. Noninvasive cardiac output assessment during moderate exercise: Pulse contour compared with co2 rebreathing. Clin. Physiol., 19:230-237, 1999.

[23] Imholz, B. P. M., W. Wieling, G. A. van Montfrans, and K. H. Wesseling. Fifteen years experience with finger arterial pressure monitoring: Assessment of the technology. Cardiovasc. Res., 38:605-616, 1998.

[24] Jones, W. B., L. L. Hefner, W. H. Bancroft, and W. Klip. Velocity of blood flow and stroke volume obtained from the pressure pulse. J. Clin. Invest., 38:2087-2090, 1959.

[25] Kenner, T. Arterial blood pressure and its measurement. Basic Res. Cardiol., 83(2):107-121, 1988.

[26] Kouchoukos, N. T., L. C. Sheppard, and D. A. McDonald. Estimation of stroke volume in the dog by pulse-contour method. Circ. Res., 26:611-623, 1970.

[27] Levett, J. M. and R. L. Replogle. Thermodilution cardiac output: a critical analysis and review of the literature. J. Surg. Res., 27:392-404, 1979.

[28] Linton, N. W. F. and R. A. F. Linton. Estimation of changes in cardiac output from the arterial blood pressure signal in the upper limb. Br. J. Anaesth., 86:486496, 2001.

[29] Ljung, L. System Identification: Theory for the User. PTR Prentice Hall, Englewood Cliffs, N.J., 1987.

[30] Martin, J. F., L. B. Volfson, V. V. Kirzon-Zolin, and V. G. Schukin. Application of pattern recognition and image classification techniques to determine continuous cardiac output from the arterial pressure signal. IEEE Trans. Biomed. Eng., 41(10):913-920, 1994.

[31] McDonald, D. A. The relation of pulsatile pressure to flow in arteries. J. Physiol, 127:533-552, 1955.

[32] McDonald, D. A. and W. W. Nichols. Left ventricular output derived from the time-derivative and phase velocities of the aortic pressure wave. Med. Biol. Eng., 11(6):678-690, 1973.

[33] Nichols, W. W. Continuous cardiac output derived from the aortic pressure signal: a review of current methods. Biomed. Eng., 8(9):376-379, 1973.

[34] Osborn, J. J., J. A. G. Russell, J. Beaumont, P. deLanerolle, B. McChesney, and F. Garfield. The measurement of relative stroke volume from aortic pulse contour pulse pressure. Vasc. Dis., 5(3):165-177, 1968.

[35] Perrott, M. H. and R. J. Cohen. An efficient approach to arma modeling of biological systems with multiple inputs and delays. IEEE Trans. Biomed. Eng., 43(1):1-14, 1996.

[36] Redling, J. D. and M. Akay. Noninvasive cardiac output estimation: A preliminary study. Biol. Cybern., 77:111-122, 1997.

[37] Remington, J. W. and W. F. Hamilton. The construction of a theoretical cardiac ejection curve from the contour of the aortic pressure pulse. Am. J. Physiol., 144:546-556, 1945.

[38] Robin, E. D. Death by pulmonary artery flow-directed catheter (editorial). time for a moratorium? Chest, 92(4):727-731, 1987.

[39] Starmer, C. F., P. A. McHale, F. R. Cobb, and J. C. Greenfield. Evaluation of several methods for computing stroke volume from central aortic pressure. Circ. Res., 33:139-148, 1973.

[40] Starr, I., T. G. Schnabel, S. I. Askovitz, and A. Schild. Studies made by simulating systole at necropsy. iv. on the relation between pulse pressure and cardiac stroke volume, leading to a clinical method of estimating cardiac output from blood pressure and age. Circulation, 9:648-663, 1954.

[41] Tajimi, T., K. Sunagawa, A. Yamada, Y. Nose, A. Takeshita, Y. Kikuchi, and M. Nakamura. Evaluation of pulse contour methods in calculating stroke volume from pulmonary artery pressure curve (comparison with aortic pressure curve). Eur. Heart J., 4:502-511, 1983.

[42] Verdouw, P. D., J. Beaune, J. Roelandt, and P. G. Hugenholtz. Stroke volume from central aortic pressure? a critical assessment of the various formulae as to their clinical value. Basic Res. Cardiol., 70:377-389, 1975.

[43] Warner, H. R. The role of computers in medical research. JAMA, 196:944-949, 1966.

[44] Warner, H. R., H. J. C. Swan, D. C. Connolly, R. G. Tompkins, and E. H. Wood. Quantitation of beat-to-beat changes in stroke volume from the aortic pulse contour in man. J. Appl. Physiol, 5:495-507, 1953.

[45] Webster, J. G. Measurement of flow and volume in blood. In J. G. Webster, editor, Medical Instrumentation. Application and Design. Houghton Mifflin Company, Boston, Mass., 1992.

[46] Welkowitz, W., Q. Cui, Y. Qi, and J. B. Kostis. Noninvasive estimation of cardiac output. IEEE Trans. Biomed. Eng., 38(11):1100-1105, 1991.

[47] Wellstead, P. E. and J. M. Edmunds. Least-squares identification of closed-loop systems. Int. J. Control, 21(4): 689-699, 1975.

[48] Wesseling, K. H., J. R. C. Jansen, J. J. Settels, and J. J. Schreuder. Computation of aortic flow from pressure in humans using a nonlinear, three-element model. Am. J. Physiol., 74(5):2566-2573, 1993.

[49] Wesseling, K. H., B. D. Wit, J. J. Settels, J. R. C. Jansen, and J. J. Schreuder. A simple device for the continuous measurement of cardiac output. its model basis and experimental verification. Adv. Cardiovasc. Phys, 5:16-52, 1983.

[50] Womersley, J. R. Method for the calculation of velocity, rate of flow and viscous drag in arteries when the pressure gradient is known. J. Physiol., 127:553-563, 1955.

[51] Antonelli L, Khanmlach R. Wavelet transform analysis of the arterial pressure signal. Computers in Cardiology 1994:568-571.

[52] Aboy M, Crespo C, McNames J, et al. Automatic detection algorithm for physiologic pressure signal components. Proc 2nd Joint EMBS/BMES Conference 2002:196-197.

[53] Navakatiyan M A, Barrett C J, Head G A, et al. A real-time algorithm for the quantification of blood pressure signals. IEEE Trans. Biomed. Eng. 2002; 49(7):662-670.

[54] Arthur C. Guyton, "Textbook of Medical Physiology", 1976, W. B. Saunders Company, Philadeophia, London, Toronto.

We claim:

1. An apparatus for determining cardiac output to within a constant scale factor comprising a computer system that includes:
   (a) computer readable media having code comprising computer-executable process steps; and
   (b) a processor that executes the process steps to:
      (i) accept an input representing a measurement of an arterial blood pressure signal over a plurality of cardiac cycles;
      (ii) estimate a function that represents the response of the arterial blood pressure to a single cardiac contraction;
      (iii) fit the function of step (ii) to an exponential-like function over a time period that begins a selected amount of time following the maximum value of the function;
      (iv) estimate the time constant of the function of step (ii) as the time constant of the exponential function of step (iii); and
      (v) determine cardiac output to within a constant scale factor by dividing average arterial blood pressure by the time constant obtained in step (iv).

2. The apparatus of claim 1, further comprising an analog-to-digital converter.

3. The apparatus of claim 1, wherein the apparatus includes a buffer system.

4. The apparatus of claim 1, wherein the apparatus includes a display device.

5. The apparatus of claim 1 wherein arterial blood pressure is measured invasively or non-invasively at any site in the systemic or pulmonary arterial tree.

6. The apparatus of claim 1 wherein arterial blood pressure is further defined as systemic arterial pressure.

7. The apparatus of claim 1 wherein arterial blood pressure is further defined as pulmonary blood pressure.

8. An apparatus for determining cardiac output to within a scale factor comprising a computer system that includes:
   (g) computer readable media having code comprising computer-executable process steps; and
   (h) a processor that executes the process steps to:
      i. accept an input representing a measurement of an arterial blood pressure signal over a plurality of cardiac cycles;
      ii. capture long time scale information by estimating an impulse response which when convolved with cardiac contractions fits the arterial blood pressure signal;
      iii. obtain a time constant by fitting an exponential-like function to the estimated impulse response over a time period that begins a selected amount of time following its maximum value;
      iv. determine cardiac output to within a scale factor by dividing a measure of the average arterial blood pressure by the time constant.

9. The apparatus of claim 8 further comprising an analog-to-digital converter.

10. The apparatus of claim 8 wherein the apparatus includes a buffer system.

11. The apparatus of claim 8 wherein the apparatus includes a display device.

12. The apparatus of claim 8 wherein arterial blood pressure is measured invasively or non-invasively at any site in the systemic or pulmonary arterial tree.

13. The apparatus of claim 8 wherein arterial blood pressure is further defined as systemic arterial pressure.

14. The apparatus of claim 8 wherein arterial blood pressure is further defined as pulmonary blood pressure.

* * * * *